United States Patent [19]

Jelly

[11] Patent Number: Plant 5,632

[45] Date of Patent: Jan. 14, 1986

[54] ROSE PLANT NAMED JELPIROFOR

[75] Inventor: Robert G. Jelly, Richmond, Ind.

[73] Assignee: E. G. Hill Co., Inc., Richmond, Ind.

[21] Appl. No.: 610,820

[22] Filed: May 15, 1984

[51] Int. Cl.[4] ..... A01H 5/00

[52] U.S. Cl. ..... Plt./14

[58] Field of Search ..... Plt./14

*Primary Examiner*—Robert E. Bagwill

*Attorney, Agent, or Firm*—Charles W. Rummler

[57] ABSTRACT

A new variety of tea rose distinguished by its very large, fully double white flowers borne on strong, fairly long stems, the blooming habit being abundant and continuous in greenhouse, the plant having a particularly vigorous vegetation and growth habit particularly suitable for greenhouse production for cut flowers.

15 Drawing Figures

BACKGROUND OF THE NEW PLANT

This new rose variety was originated at Richmond, Ind., as a seedling resulting from my crossing of two selected rose plant varieties with the object of producing large, well shaped flowers of white color on plants having a strong and vigorous growth habit particularly suitable for greenhouse culture for the production of cut flowers. This particular seedling was selected for reproduction because it came the closest to my breeding objectives and was propagated by bud grafting through several successive generations at Richmond, Ind., which demonstrated that the novel characteristics of the parent seedling were fully retained from generation to generation of its clones and appeared to be firmly fixed. Plants of this new rose variety are grown at Richmond, Ind., and are cultivated under glass for the European market at Le Cannet, Des Maures, Var, France.

DESCRIPTION OF THE DRAWING

This new variety of tea rose is illustrated by the accompanying full color photographic drawing which shows the distinctive elements of the new plant and in which.

DESCRIPTION OF THE NEW PLANT

Figures 1, 2, 3, 4, 5, 6, 7, 8, 9, 10, 11, 12, 13, 14, 15:
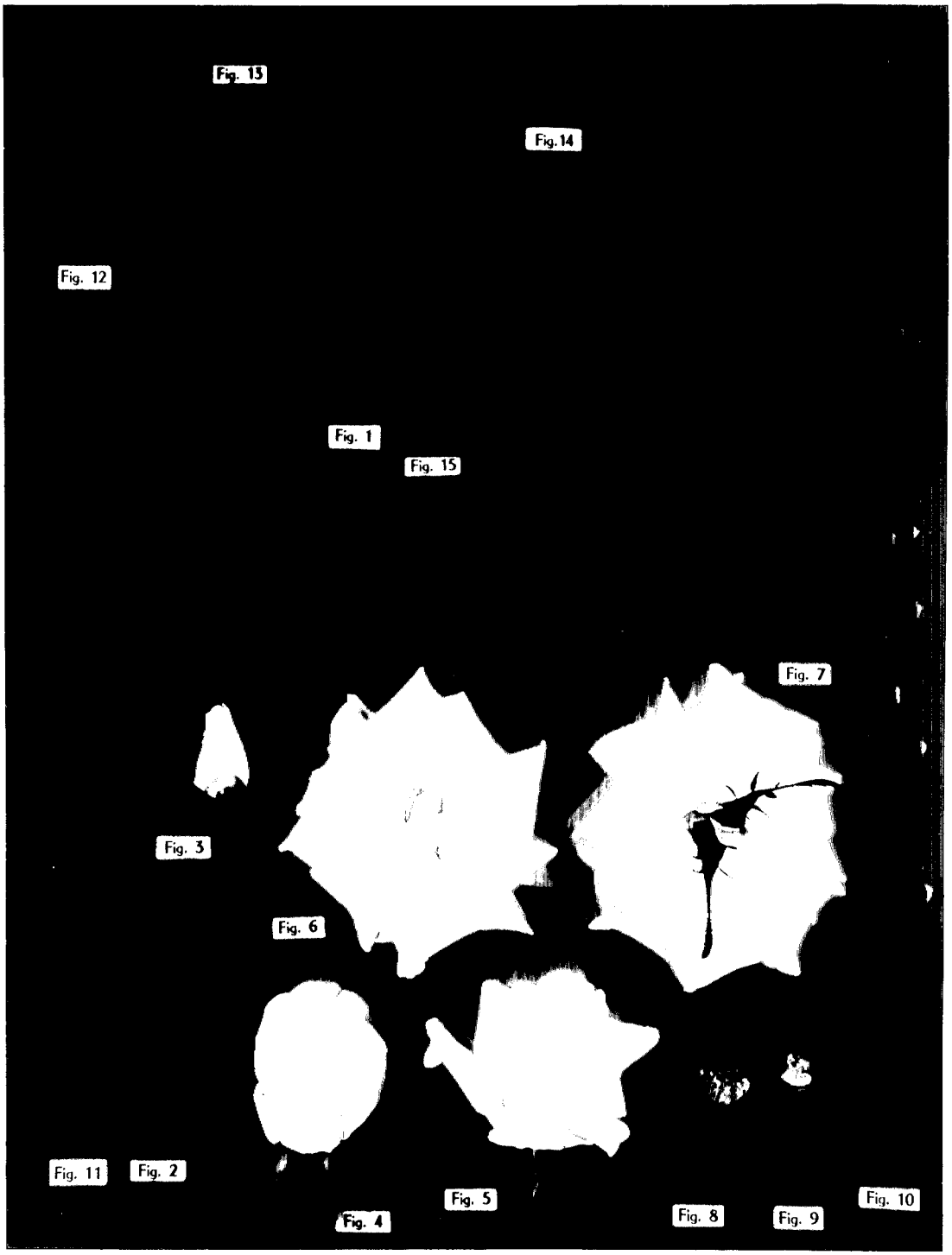
FIG. 1 shows a young shoot.
FIG. 2 shows a bud before the sepals burst open.
FIG. 3 shows a bud at the opening of the sepals.
FIG. 4 shows the flower at the beginning of opening.
FIG. 5 shows a flower in the course of opening.
FIG. 6 is a face view of a fully blown flower.
FIG. 7 is a back or stem-side view of a fully blown flower.
FIG. 8 is a view of the floral receptacle showing the disposition of stamens (sepals and petals being removed)
FIG. 9 is a view of the floral receptacle showing the disposition of the pistils (sepals, petals and stamens having been removed)
FIG. 10 shows a portion of mature wood.
FIG. 11 shows a portion of young stem.
FIG. 12 shows the upper surface of a leaf with one leaflet.
FIG. 13 shows the upper side of a leaf having three leaflets.
FIG. 14 shows the upper surface of a leaf having five leaflets.
FIG. 15 shows the under surface of a leaf having seven leaflets.

The following is a detailed description of my new rose plant as observed on plants being grown under glass at Le Cannet, Des Maures, France, and observed in October, the color designations being according to The R.H.S. Colour Chart of The Royal Horticultural Society at London, England.

THE PLANT

Origin: Seedling.

Parentage:

*Seed parent.*—"Bridal Pink" (U.S. Plant Pat. No. 2,851).

*Pollen parent.*—An unnamed seedling of unknown parentage.

Classification: Hybrid tea rose.

Form: An erect bush.

Height: On the basis of cutting back of the plants in greenhouse to about 85 cm., the length of the flower stems settles generally between 60 to 80 cm.

Growth: Vigorous and upright.

Branches: Normal.

*Young stems.*—Color: Bronze Green 146A.

*Mature wood.*—Color: Bronze Green 146A.

*Prickles.*—Size: Medium but very long. Quantity: Fairly numerous and sometimes intermixed with numerous glands. Shape: Upper edge — Straight to slightly convex and extremely slim. Under edge — Concave. Color: On young stems — Reddish. On mature wood — Havana.

Foliage:

*Quantity.*—Abundant.

*Form of leaf.*—Odd pinnate.

*Leaflets.*—Number: 1, 3, 5, 7 more often, and occasionally 9. Shape: Generally elliptical and somewhat lanceolate with plain and regularly serrated margin. Texture: Leathery. Color: Young Foliage: Upper surface — Dark Green 147A. Under surface — Light Green 148C. Mature Foliage: Upper surface — Dark Green 147A. Under surface — Medium Green 148B. Stipules: Adnate, quite pectinate, wide and linear. Petioles: Inner surface: Grooved, with reddish brown edges and most glandular. Outer surface: Light green, bearing some small hooked prickles.

THE BUD

Size: Medium.

Shape: Long ovoid before opening of the sepals.

Length: 3.7 cm. on average, outside the calyx, at the opening of the sepals.

Color of petals: On opening: Both upper and under surface, in the very close bud, Bluish Yellow 154D becoming Sappy Green afterwards, 150D.

Sepals:

*Upper surface.*—Tomentous greenish.

*Under surface.*—Light green, slightly glandular. The outside sepals have their edges a little appendiculate and are sometimes stained reddish along a middle line.

*Character.*—Sepals turn outwardly and downwardly as the bud opens.

Puduncle:

*Length.*—Fairly long with very sharp top and fairly glandular edges.

*Character.*—Erect and rigid, light green in color slightly shaded reddish brown, fairly tomentous and glandular, and bearing some tiny prickles.

THE FLOWER

Blooming habit: Generally uniflorous; however, in forced culture, the two first axillary eyes below the flower sometimes develop.

Size of bloom: Large.

*Diameter.*—15 cm. on average.

*Shape.*—Parallel sides, well turbinate.

Chorisis: Fully double.

Petalage:

*Number.*—55 on average.

*Arrangement.*—Imbricated.

*Shape.*—Outside petals are rounded and very wide. Inside petals are ovoid and narrow; at their apex, the petals generally present a small peak; the tiny unguis is greenish on both faces of all petals.

Fragrance: None.

Persistence: The petals drop off cleanly.

Lasting quality:

*As cut flowers.*—A relatively long time.

REPRODUCTIVE ORGANS

Stamens:

*Number.*—190 on average.

*Anthers.*—Color: Ochre-yellow, sometimes slightly fuchsine shaded at the center.

*Filaments.*—Yellowish.

Pistils:

*Number.*—137 on average.

*Styles.*—Fuchsine with greenish base, more or less tomentous and slightly twisted.

*Stigmas.*—Whitish.

Receptacle:

*Color.*—Light green at the dehiscence of the anthers; in longitudinal section, it is in the form of a rather narrow jug.

This new variety of rose plant has a very vigorous growth habit and produces large, particularly smart, fully double white flowers, and is particularly suited for greenhouse culture for the production of cut flowers.

I claim:

1. A new and distinct hybrid tea rose plant, substantially as herein shown and described, particularly distinguished by its large, fully double flowers of white color.

* * * * *